(12) United States Patent
Mittelstein et al.

(10) Patent No.: US 7,842,034 B2
(45) Date of Patent: Nov. 30, 2010

(54) ELECTROSURGICAL DEVICES AND METHODS FOR SELECTIVE CUTTING OF TISSUE

(75) Inventors: Michael Mittelstein, Laguna Niguel, CA (US); John T. Sorensen, Lake Elsinore, CA (US); Soheila Mirhashemi, Laguna Niguel, CA (US); James B. Gerg, Lake Forest, CA (US)

(73) Assignee: Neomedix Corporation, Tustin, CA (US)

( * ) Notice: Subject to any disclaimer, the term of this patent is extended or adjusted under 35 U.S.C. 154(b) by 457 days.

(21) Appl. No.: 10/560,265

(22) PCT Filed: Jun. 10, 2004

(86) PCT No.: PCT/US2004/018482

§ 371 (c)(1),
(2), (4) Date: Aug. 7, 2006

(87) PCT Pub. No.: WO2004/110259

PCT Pub. Date: Dec. 23, 2004

(65) Prior Publication Data

US 2007/0010812 A1 Jan. 11, 2007

Related U.S. Application Data

(60) Provisional application No. 60/477,258, filed on Jun. 10, 2003.

(51) Int. Cl.
*A61B 18/14* (2006.01)

(52) U.S. Cl. .............................. 606/48; 606/41; 606/50

(58) Field of Classification Search .................. 606/41, 606/48–50
See application file for complete search history.

(56) References Cited

U.S. PATENT DOCUMENTS

| 5,269,782 | A | | 12/1993 | Sutter | |
|---|---|---|---|---|---|
| 5,458,596 | A | * | 10/1995 | Lax et al. | 606/31 |
| 5,681,282 | A | * | 10/1997 | Eggers et al. | 604/114 |
| 5,885,279 | A | * | 3/1999 | Bretton | 606/41 |
| 6,068,629 | A | * | 5/2000 | Haissaguerre et al. | 606/41 |
| 6,283,961 | B1 | * | 9/2001 | Underwood et al. | 606/41 |
| 6,290,699 | B1 | * | 9/2001 | Hall et al. | 606/41 |
| 6,432,104 | B1 | * | 8/2002 | Durgin et al. | 606/45 |
| 6,979,328 | B2 | | 12/2005 | Baerveldt et al. | |
| 7,244,256 | B2 | * | 7/2007 | DeCesare et al. | 606/41 |
| 2002/0002372 | A1 | * | 1/2002 | Jahns et al. | 606/41 |

* cited by examiner

*Primary Examiner*—Michael Peffley
(74) *Attorney, Agent, or Firm*—Robert D. Buyan; Stout, Uxa, Buyan & Mullins

(57) ABSTRACT

Methods and devices for cutting or coagulating. A device comprises a) an elongate member having a distal end, b) at least one foot member extending from the distal end of the elongate member, said foot member having a upper surface and a lower surface, c) an electrically and thermally insulating covering formed on at least the lower surface of the foot member and d) at least one electrode on the upper surface of the foot member. In operation, the at least one electrode is energized so as to cause cutting or coagulation of tissue located above the upper surface(s) of the foot member(s) while not causing substantial damage to tissue located below the lower surface(s) of the foot member(s).

33 Claims, 2 Drawing Sheets

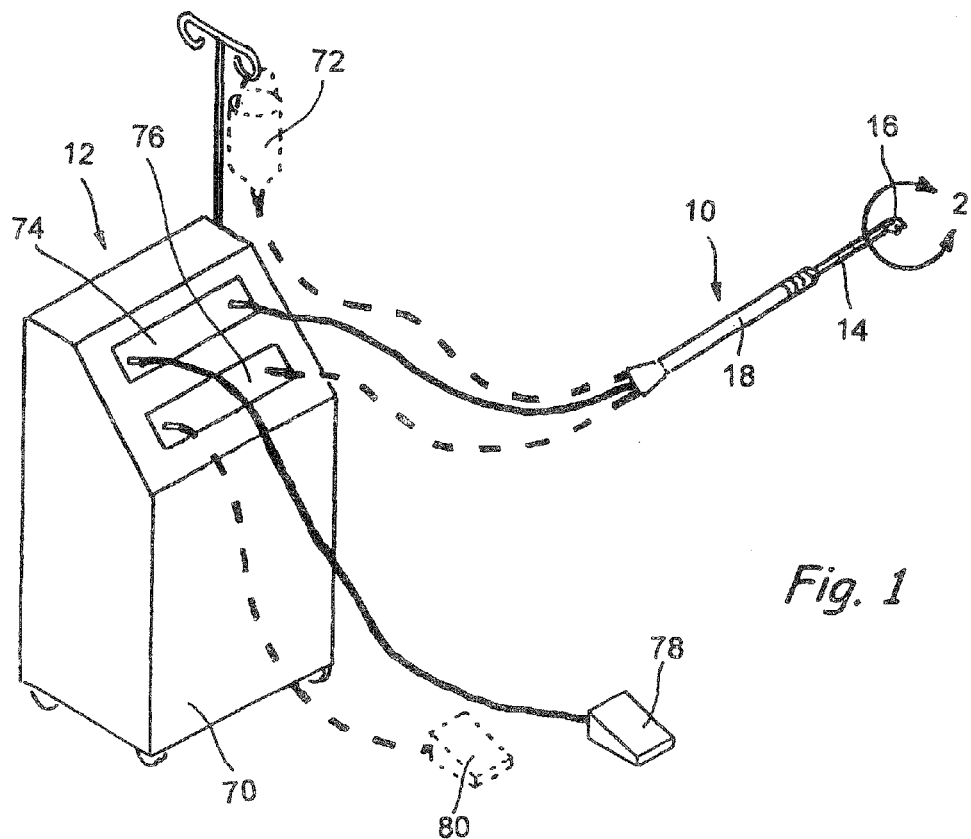
Fig. 1
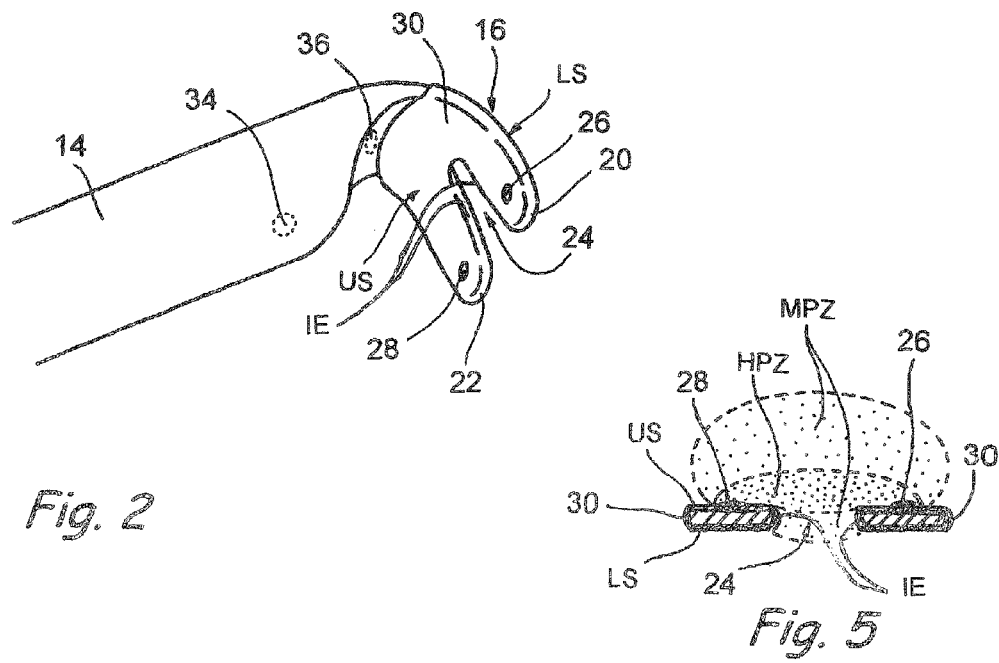
Fig. 2
Fig. 5

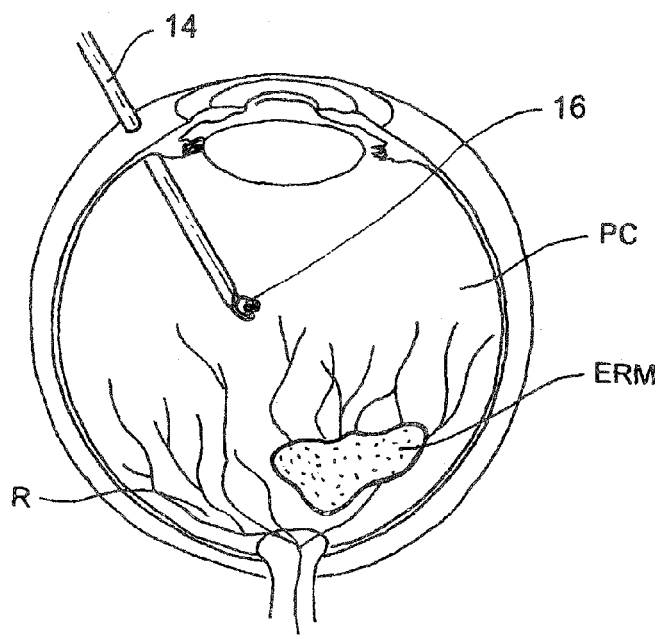
Fig. 3
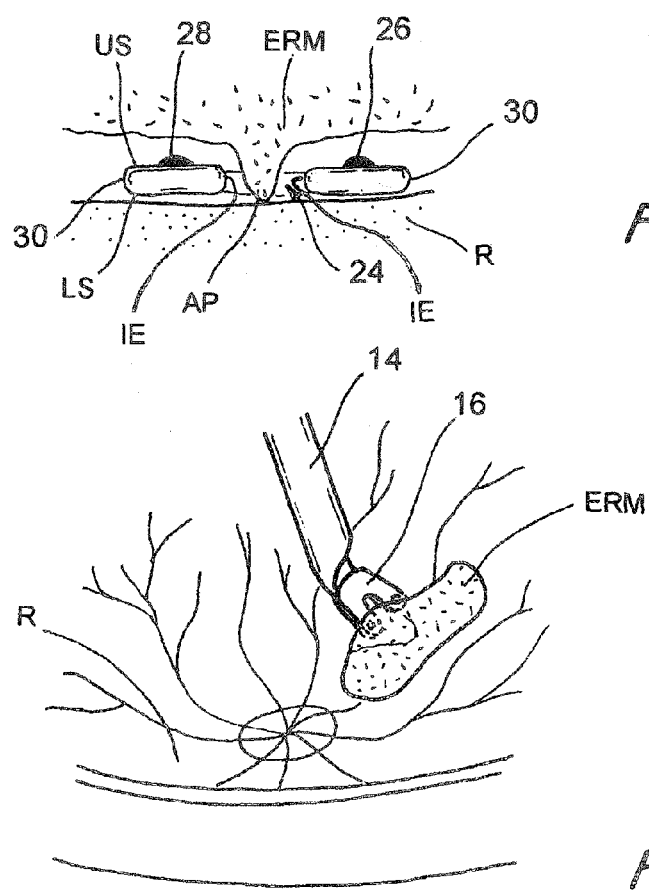
Fig. 4A
Fig. 4

ELECTROSURGICAL DEVICES AND METHODS FOR SELECTIVE CUTTING OF TISSUE

RELATED APPLICATIONS

This application claims priority to U.S. Provisional Patent Application No. 60/477,258 filed on Jun. 10, 2003, the entirety of which is expressly incorporated herein by reference.

BACKGROUND OF THE INVENTION

There are numerous medical and surgical procedures wherein el electrosurgical probes are used to cut and/or cauterize tissue. Numerous monopolar and bipolar electrosurgical probes are available on the market today. Electrosurgical probes typically comprises a probe tip that is permanently or releasably attached to a handpiece. The handpiece is sized and configured to be grasped by the human hand. The probe tip typically extends distally from the handpiece. The distal end of each probe tip typically has a specific shape (e.g., straight, curved, hook shaped, looped, square, ball, spatula, needle, ball, L-shaped, forceps, clamps, etc.). The probe tip typically incorporates one or more electrodes that, when energized, cause the probe tip to heat. The handpiece may be adapted for connection to an electrosurgical signal generator, which provides energy to heat the probe tip. In some cases, insulation may surround all but the distal-most end of the probe tip to prevent peripheral tissue damage or capacative couplance. In many cases, the temperature of the probe tip is variable and may be controlled by a rheostat or other apparatus for varying the amount of electrical current that passes through the electrode(s) at the probe tip. Examples of electrosurgical generators, handpieces and/or probe tips include those that are commercially available from Bovie Medical Corporation, St. Petersburg, Fla.; Hi-Top/W. J. Surgical, Elizabethtown, Pa., ValleyLab Division of Tyco Healthcare Group LP, Boulder, Colo. and ProSurg, Inc., San Jose, Calif.

While the electrosurgical probes of the prior art have been used to cut many different types of tissue, there are still certain surgical procedures wherein electrosurgical probes have not been used due to concerns about inadvertent burning or damaging delicate nearby tissues.

One example of a procedure that has heretofore not typically been performed using electrosurgical devices is the removal of epiretinal membranes from the eye. An epiretinal membrane (sometimes referred to as macular pucker, premacular fibrosis or surface-wrinkling retinopathy) is an abnormal, transparent or translucent, collagen-containing membrane that forms between the inner limiting membrane of the retina and the cortex of the vitreous body. As the epiretinal membrane contracts, it causes the retina to become distorted or wrinkled thereby disturbing the patient's vision. Visual symptoms may vary from very mild symptoms to very severe symptoms. Patients may experience blurred vision or loss of central acuity. Patients may also experience distorted vision In which straight lines appear to be bent or curved; or objects appear to be distorted in shape and form. Rarely, epiretinal membranes can damage the retina so severely that the patient can almost lose central vision and only see with their peripheral vision.

The treatment epiretinal membrane generally involves surgery to remove the epiretinal membrane. In such surgery, an ophthalmologic surgeon initially performs a vitrectomy wherein a vitrectomy cutter is used to remove the vitreous body from the posterior chamber of the eye. After the vitreous body has been removed, the surgeon gently peels the epiretinal membrane off of the surface of the retina using fine instruments. The epiretinal membrane may be attached to the retina at discrete attachment points. Thus, the peeling of the membrane from the retina can result In some undesirable tugging or traction on the retina with potential tearing and bleeding of the retina, or even local detachment of the retina. After the epiretinal membrane has bees successfully removed, the macula typically flattens out and the patient's symptoms slowly improve. The majority of patients get improvement of vision following the operation, however some distortion of vision and/or loss of visual acuity may remain post-surgically.

At present there remains a need in the art for the development of new electrosurgical devices that provide for control over the area In which heat generated by the device can cause substantial cutting and/or coagulation of tissue, thereby elimination unwanted collateral damage during the procedure.

SUMMARY OF THE INVENTION

The present invention provides device for cutting or coagulating tissue which comprises, consists of or consists essentially of a) an elongate member having a distal end, b) at least one foot member extending from the distal end of the elongate member, said foot member having a upper surface and a lower surface, c) an electrically and thermally insulating covering formed on at least the lower surface of the foot member and d) at least one electrode on the upper surface of the foot member. In operating, the at least one electrode may be energized so as to cause cutting or coagulation of tissue located above the upper surface(s) of the foot member(s) while not causing substantial damage to tissue located below the lower surface (s) of the foot member(s). The foot member(s) may comprise a single foot member, a plurality of foot members separated by open area(s) or a single foot member that is furcated or branched into a plurality of foot member portions that are separated by open area(s) therebetween. The device may, in some embodiments, incorporate one or more lumen(s) for infusion and/or aspiration of fluid and/or matter. In some embodiments, the device may be formed on, attached to or passed through a lumen or channel of a cannula, flexible catheter (e.g., percutaneously insertable catheter) or endoscopic device. In some embodiments, the insulating covering may cover the upper surface(s) of the foot member(s) or the entire surface(s) of the foot member(s). The insulating covering may comprise a coating, such as a polymer (e.g., polyimide) coating. The electrode(s) may be bipolar or monopolar.

Further in accordance with the present invention, there is provided a method for selective electrosurgical cutting or coagulation of tissue, such method comprising the steps of; a) providing a device which comprises i. an elongate member having a distal end, ii. at least one foot member extending from the distal end of the elongate member, said foot member having a upper surface and a lower surface, iii. an electrically and thermally insulating covering formed on at least the lower surface of the foot member; and iv. at least one electrode on the upper surface of the foot member; b) positioning the device such that tissue that is to be cut or coagulated is located above the upper surface of the at least one foot member and other tissue is located below the lower surface of the at least one foot member, and c) energizing the at least one electrode such that tissue located above the upper surface of the at least one foot member is cut or coagulated and tissue that is located below the lower surface of the at least one foot member is not substantially cut or coagulated. In some applications of the method the device may be formed on or attached to a handpiece. In some the device may be formed on, attached to or passed through a lumen or channel of a cannula, flexible catheter or endoscopic device.

Further aspects and elements of the invention will be understood by those of skill in the art upon reading the detailed description of specific examples set forth herebelow.

BRIEF DESCRIPTION OF THE DRAWINGS

FIG. 1 is a perspective view of a system incorporating an electrosurgical tissue cutting device of the present invention.

FIG. 2 is an enlarged perspective view of section 2 of FIG. 1.

FIGS. 3-4A show several steps in a method for using an electrosurgical probe of the present invention to remove an epiretinal membrane from the eye of a human or animal subject.

FIG. 5 is a cross-sectional view of the distal end of an electrosurgical probe of the present invention illustrating the power zones that are present when the device is in use.

DETAILED DESCRIPTION

The following detailed description, and the drawings to which it refers, are provided for the purpose of describing and illustrating certain preferred embodiments or examples of the invention only, and no attempt has been made to exhaustively describe all possible embodiments or examples of the invention. Thus, the following detailed description and the accompanying drawings shall not be construed to limit, in any way, the scope of the claims recited in this patent application and any patent(s) issuing therefrom.

FIGS. 1-2 and 5 show an example of one embodiment of a device for cutting or coagulating tissue in accordance with the present invention. The device 10 shown in these figures comprises an elongate member 14 having a foot member 16 formed on its distal end. The foot member 16 is bifurcated or divided, as shown, into a first (or right) foot member portion 22 and a second (or left) foot member portion 20, each of which has an upper surface US, an inner edge IE and a lower surface LS. As seen in at least FIGS. 2, 4, 4A and 5, the inner edges IE of the right and left foot member portions 20, 22 are juxtaposed to each other and an open area 24 exists therebetween. An electrically and thermally insulating covering 30 is formed on the foot member 16. In this example, the insulating covering 30 covers the entire foot member 16 including the upper US and lower LS surfaces thereof. It will be appreciated, however, that in some embodiments of the device 10 the insulating covering 30 may be disposed only on the lower surface LS of the foot member 16 or only on the lower surfaces LS of the foot member portions 22, 20. As may be seen in the cross section of FIG. 5, the foot member 16 may be formed of conductive core material such as metal (e.g., medical grade stainless steel) and the covering 30 may be formed of a coating disposed on the surface of the core material. The coating that forms the insulating covering 30 may comprise a dielectric polymer such as polyimide and may be applied by any suitable means including but not limited to; single layer dip coating, multi layer dip coating, painting, powder coating (e.g., electro static), vapor deposition, etc.

At least one electrode is located on the upper surface US of the foot member 60. The device 10 shown In this example is bipolar, so a first electrode 28 is located on the upper surface of the first foot member portion 22 and a second electrode 26 is located on the upper surface of the second foot member portion 20. When energized, these electrodes will create a tissue damaging thermal zone above the upper surface US of the foot member 60 as well as above and somewhat Into the open area 24 that exists between the first and second foot member portions 22, 20. As illustrated in FIG. 5, when the electrodes 26, 28 are energized, the tissue damaging thermal zone above the above the upper surface US will actually comprise a high power zone HPZ and a medium power zone MPZ, both of which are sufficient to cut or coagulate tissue. Thus, the effective tissue damaging thermal zone will include both the high power zone HPZ and the medium power zone MPZ.

As shown In FIG. 2, the device 10 may optionally include one or more lumens that extend through the elongate member 14 and terminate in apertures 34, 36 such that fluid or matter may be infused and/or aspirated through the device. In some embodiments two (2) lumens (not shown) may be included and those lumens may terminate in two separate apertures 34, 36, thereby allowing for simultaneous Infusion and aspiration through the device 10.

The device 10 of the present invention may optionally be used as part of a system 12, one example of which is shown in FIG. 1. The basic components of this system 12 include an includes an electrical current source, such as an electrosurgical generator 76 and electrosurgical foot pedal 80 which controls the electrosurgical generator to deliver desired amount(s) of energy to the electrode(s) 26, 28 on the device 10. If the device 10 includes optional aspiration and/or infusion lumen(s), the system 12 may additionally include an aspiration pump module 74 and aspiration foot pedal 78 and/or a source of Irrigation fluid 72. These components of the system may be independent or may be mounted on a surgical roller cart 70, as shown. Control of the system functions during procedures may be accomplished by moving the electrosurgical foot pedal 80 which controls the electrosurgical generator to deliver desired amount(s) of energy to the electrode(s) 26, 28 and, optionally, moving the aspiration foot pedal 78 to control the aspiration pump 74 and/or varying the height of the source of infusion fluid 72 to change the gravity fed pressure or flow rate of infusion fluid through the optional infusion lumen of the device 10. In some embodiments, footpedals 78, 80 may be combined into a single multifunctional unit. A pinch valve, or other means, may also be incorporated In the console to control flow of the irrigation fluid to the device 10. As an option, all of the basic control functions of system 12 may be integrated into a single footpedal to facilitate use.

The device 10 may be provided as a pre-sterilized, single-use disposable probe or tip that is attachable to a standard electrosurgical handpiece 18. Alternatively it may be permanently attached to or formed integrally of a handpiece, cannula, catheter, endoscope or other apparatus.

The device 10 and system 12 are useable to perform a variety of procedures wherein it is desired to EXAMPLES OF METHODS WHEREIN THE DEVICE OF THE PRESENT INVENTION IS USED TO SELECTIVELY CUT OR COAGULATE TISSUE 1) Detachment of Retinal Membrane Overgrowths in the Posterior Segment of the Eye One example of a method of the present invention is the use of the above-described device to remove an epiretinal membrane from the eye of a human or animal subject. Certain steps of this method are shown in FIGS. 3-4A.

With reference to FIGS. 3-4A, in this example, the epiretinal membrane ERM is an abnormal, transparent or translucent, collagen-containing membrane that is formed between the inner limiting membrane of the retina R and the cortex of the vitreous body which fills the posterior chamber PC of the eye. This epiretinal membrane is adhered or attached to the retina R at discrete adhesion points AP. Thus, because of these adhesion points AP, as the epiretinal membrane contracts, it will create traction on the retina causing the retina to become distorted or wrinkled and thereby disturbing the patient's vision.

To remove the epiretinal membrane ERM in this example, the ophthalmologic surgeon initially performs a vitrectomy wherein a vitrectomy cutter is used to remove the vitreous body from the posterior chamber PC of the eye in accordance with well known technique. After the vitreous body has been removed, the surgeon will Insert the device 10 of the present invention into the posterior chamber as shown in FIG. 3 and will advance the device 10 to a position, as shown in FIGS. 4 and 4A, where an adhesion point AP extends through the open area 24 between the first and second foot portions 22, 20, the remainder of the epiretinal membrane ERM is above the upper surface US of the foot portion 16 and the retina R is below the lower surface LS of the foot portion 16. With the device 10 so positioned, the electrodes 26, 28 are energized to cause cutting or destruction of the portion of the epiretinal membrane ERM located at the adhesion point AP while the foot member portions 22, 20 and insulating cover 30 substantially protect the retina R from electrical or thermal damage during energization of the electrodes 22, 20. This procedure is repeated for each adhesion point AP located, thereby releasing the epiretinal membrane ERM from the retina R and enabling the surgeon to proceed with removal of the epiretinal membrane ERM in accordance with standard technique without undesirable tugging or traction on the retina with potential tearing, bleeding or even local detachment of the retina. Thus, the procedure may be accomplished with decreased potential for retinal tears, bleeding or other trauma.

Although FIGS. 3-4A specifically show a method for detaching an epiretinal membrane, it will be appreciated that the device 10 may be used in a substantially similar manner as described elsewhere in this application to perform a wide variety of procedures wherein tissue is to be selectively cut or coagulated without causing substantial damage to neighboring tissues. Some examples of these other methods wherein the device 10 is used are described in the additional examples set forth herebelow.

2) Selective Cauterization of Retinal Vessels in the Posterior Segment of the Eye As a result of certain diseased states, often related to diabetes, retinal vascular abnormalities can occur. Initially, diabetic retinopathy often involves weakening and bleeding from retinal vessels. In later stages, new vessels often begin to proliferate and even grow into the vitreous, obscuring vision. Treatment often involves focal laser photocoagulation, where a laser is used to create tiny spots of photocoagulation, either directed or scattered across the retina. The device 10 and/or system 12 of the present invention could provide an effective means of selectively coagulating vessels of the retina or extending from the retina while limiting the thermal trauma to adjacent retinal tissue.

3) Gum/Oral Surgery Dissection

Often dental procedures and oral surgical procedures involve gum dissection. These dissections are often performed near teeth, roots, nerves, or other sensitive structures. In addition, gum tissue is highly vascularized and cutting leads to significant bleeding. The device 10 and/or system 12 of the present invention could provide a superior means for cutting of gum tissue while protecting adjacent sensitive tissues and structures and reducing bleeding.

4) Dermatology Procedures

Dermatology procedures involve selective ablation of particular growths, cutting of skin where depth of trauma needs to be controlled to protect underlying tissues, and requires control of bleeding. The device 10 and/or system 12 of the present invention would provide a means for performing such procedures wherein the energy could be applied in such a manor as to provide distinct advantages for said procedures.

5) Selective Ablation/Removal of Tumors or Other Tissue Growths

Cancerous tumors and other abnormal tissue growths often challenging or deemed "inoperable" because of being located adjacent to or too intimately with vital organs or sensitive tissues. The device 10 and/or system 12 of the present invention would provide surgeons with a means for better directing the energy used for tumor ablation and removal allowing for such procedures to be better performed in the vicinity of vital organs or sensitive tissues. In addition, such procedures could also be performed with less trauma to adjacent normal tissues, even if they are not particularly vital or sensitive, reducing healing time and limiting the local trauma. Tumors or non-cancerous growths such as some dermatological lesions that are pedunculated may be removed using the device 10 by positioning the device 6) Brain and Neurological Surgical Procedures Neurological procedures and brain surgery often involve delicate tissue cutting and/or removal or treatment of hemorrhagic sites in close proximity to nerves and/or sensitive tissues such as brain tissue. In these cases, The device 10 and/or system 12 of the present invention could offer the advantage of facilitating such tissue cutting and/or removal or treatment of hemorrhagic sites while minimizing trauma to such adjacent nerve or brain tissues.

7) Vocal Cord Surgery

The vocal cords are often effected by abnormal growths (e.g., nodules) that must be carefully removed while minimizing damage to the delicate vocal cords. The device 10 and/or system 12 of the present invention would offer the surgeon a superior means of removing these abnormal growths while minimizing exposure of the adjacent vocal cord tissues to trauma.

8) Heart Surgery

The device 10 and/or system 12 of the present invention may offer an effective means of cutting the membranous tissue structures of the heart, including the pericardium and endocardium or other cardiac tissue while protecting the underlying myocardium and/or the critical vascular structures that perfuse the heart or other structures (e.g., myocardium, a coronary or cardiac blood vessel, tendonous chord, papillary muscle, heart valve, trabeculae, cardiac nodal tissue, coronary venous sinus, septum or other normal cardiac tissue). Catheter-based or minimally-invasive implementations of the device 10 and/or system 12 of the present invention could also be advantageous for selective ablations (e.g., ablating arrhythmogenic pathways or tissue) and tissue or prosthetic valve procedures, valvuloplasty or anuloplasty procedures, etc.

8) Liver Dissection

Surgical procedures on the liver often require cutting of liver tissue while controlling bleeding and minimizing trauma to the larger vascular structures that crisscross the hepatic tissues in a complex array. The device 10 and/or system 12 of the present invention would offer the surgeon a superior manner of controlling bleeding while cutting through liver tissue and minimizing damage to adjacent vasculature and tissue.

9) Ear Nose and Throat (ENT) Surgical Procedures

ENT surgical procedures often involve working in small confined passageways (for example the sinuses) to cut/coagulate tissue near sensitive adjacent structures and tissues. The device 10 and/or system 12 of the present invention would offer the ENT surgeon a means for operating in very confined spaces while selectively avoiding trauma to adjacent tissues that are necessarily in close geometric proximity due to the limited operating space.

10) Arthroscopic Procedures

Arthroscopic procedures often involve tissue cutting in a wet field environment. Often it is desired to selectively cut tissue (cartilage, tendon, etc.) from adjoining structures where minimizing the trauma to said adjoining structures (for example, bone) would be desirable to facilitate healing. Also, bleeding obscures the visual field In these procedures. Thus, The device 10 and/or system 12 of the present invention could provide the arthroscopic surgeon a superior means for affecting said procedures.

11) Colonoscopy and Other Oral or Gastrointestinal Procedures

Removal of tumors, polyps and/or other growths from the gastrointestinal tract or alimentary canal for therapeutic or diagnostic (e.g., biopsy) purposes can induce unwanted bleeding and/or unintentional damage to adjacent tissue, such as bowel perforation. The device 10 and/or system 12 of the present invention can be used for cutting and/or removal of tumors, polyps and/or other growths and/or collection of biopsy samples from the walls of the alimentary canal (e.g., the rectum, colon, small intestine, duodenum, stomach, esophagus, oropharynx, tongue or oral cavity) without causing substantial bleeding, perforation of the alimentary canal or other damage to the wall of the alimentary canal. In such procedures, the device 10 may be advanced through Although the invention has been described above with respect to certain embodiments and examples, it is to be appreciated that such embodiments and examples are non-limiting and are not purported to define all embodiments and examples of the invention. Indeed, those of skill in the art will recognize that various modifications may be made to the above-described embodiments and examples without departing from the intended spirit and scope of the invention and it is intended that all such modifications be included within the scope of the following claims.

What is claimed is:

1. A device for cutting or coagulating tissue, said device comprising:
    an elongate member having a distal end;
    a bifurcated foot member extending angularly from and to one side of the distal end of the elongate member, said bifurcated foot member comprising a right foot member portion having an upper surface, an inner edge and a lower surface and a left foot member portion having an upper surface, an inner edge and a lower surface, the inner edges of the right and left foot member portions being juxtaposed to each other with an open area therebetween;
    an electrically and thermally insulating covering formed on at least the lower surfaces of the right and left foot member portions; and
    an electrode on the upper surface of the right foot member portion; and
    an electrode on the upper surface of the left foot member portion;
    wherein the electrodes are energizable to thermally cut or coagulate tissue at a location above the open space located between the inner edges of the right and left foot members, without causing substantial thermal cutting and/or coagulation of tissue located below the lower surfaces of the right and left foot members.

2. A device according to claim 1 in combination with an electrosurgical generator for energizing the electrodes.

3. A device according to claim 1 wherein the electrically and thermally insulating covering is formed on the upper and lower surfaces of the right and left foot members and wherein the electrodes are located on top of the electrically and thermally insulating covering.

4. A device according to claim 1 further comprising at least one lumen useable for infusion of fluid or matter and/or aspiration of fluid or matter.

5. A device according to claim 4 wherein the device comprises first and second lumens such that fluid or matter may be infused through one lumen while fluid or matter is aspirated through the other lumen.

6. A device according to claim 1 wherein the insulating covering comprises a coating.

7. A device according to claim 1 wherein the insulating covering comprises a polymer coating.

8. A device according to claim 7 wherein the polymer coating comprises a polyimide coating.

9. A device according to claim 1 wherein the covering comprises a coating that has been applied by a coating method selected from the group consisting of:
    single layer dip coating
    multi layer dip coating
    painting
    powder (electro statically)
    vapor deposition.

10. A device according to claim 1 further comprising a handpiece from which the elongate member extends.

11. A device according to claim 10 wherein the elongate member is releasably attached to the handpiece.

12. A device according to claim 11 wherein the elongate member is disposable and the handpiece is reusable.

13. A device according to claim 10 wherein the elongate member is permanently attached to or integrally formed with the handpiece.

14. A device according to claim 13 wherein the handpiece and elongate member are autoclavable.

15. A system comprising a device according to claim 1 in combination with a cannula through which the device is insertable.

16. A system according to claim 15 wherein the cannula comprises a rigid cannula.

17. A system according to claim 15 wherein the cannula comprises a flexible catheter or percutaneously insertable catheter.

18. A system comprising a device according to claim 1 in combination with an endoscope that is useable to view the positioning of the device within the body of a human or animal subject.

19. A system according to claim 18 wherein the endoscopic device is selected from the group consisting of:
    gastrointestinal endoscopes;

dental endoscopes;
sigmoidoscopes;
colonoscopes;
laparoscopes;
thoracoscopes;
cystoscopes; and
arthroscopes.

20. A method for selective electrosurgical cutting or coagulation of tissue, said method comprising the steps of:
  A) inserting a device which comprises;
    an elongate member having a distal end;
    a bifurcated foot member that extends angularly from, and to one side of, the distal end of the elongate member, said bifurcated foot member comprising a right foot member portion having an upper surface, an inner edge and a lower surface and a left foot member portion having an upper surface, an inner edge and a lower surface, the inner edges of the right and left foot member portions being juxtaposed to each other and an open area existing therebetween;
    an electrode on the upper surface of the right foot member portion;
    an electrode on the upper surface of the left foot member portion; and
    an electrically and thermally insulating covering formed on at least the lower surfaces of the right and left foot member portions;
  B) positioning the device such that tissue that is to be cut or coagulated is located directly above the open area that exists between said inner edges; and
  C) energizing the electrodes to thermally cut or coagulate tissue located above the open area that exists between said inner edges, without causing substantial thermal cutting and/or coagulation of tissue located below the lower surfaces of the right and left foot members.

21. A method according to claim 20 wherein the mass of tissue comprises a tumor.

22. A method according to claim 20 wherein the mass of tissue comprises a blood vessel.

23. A method according to claim 20 wherein the mass of tissue comprises an adhesion.

24. A method according to claim 20 wherein the mass of tissue comprises a gastrointestinal polyp, tumor or other growth that protrudes from a wall of the colon, small intestine, duodenum, stomach, esophagus, oropharynx or oral cavity.

25. A method according to claim 20 wherein the mass of tissue comprises a retinal blood vessel.

26. A method according to claim 20 wherein the mass of tissue comprises an epiretinal membrane.

27. A method according to claim 20 wherein the mass of tissue comprises gingival tissue.

28. A method according to claim 20 wherein the mass of tissue comprises a dermatological lesion.

29. A method according to claim 20 wherein the mass of tissue comprises neurological tissue or abnormal tissue that is attached to neurological tissue.

30. A method according to claim 20 wherein the mass of tissue comprises a nodule or other growth on a vocal chord.

31. A method according to claim 20 wherein the mass of tissue comprises pericardium, endocardium or cardiac tissue.

32. A method according to claim 20 wherein the mass of tissue comprises cartilage, tendon or ligament.

33. A method according to claim 20 wherein the device is inserted through a channel of an endoscopic device.

* * * * *